United States Patent [19]

Saari et al.

[11] Patent Number: 4,897,423
[45] Date of Patent: Jan. 30, 1990

[54] DINITROBENZENESULFONAMIDES

[75] Inventors: Walfred S. Saari, Lansdale; Edward L. Engelhardt, Gwynedd Valley, both of Pa.

[73] Assignee: Merck & Co. Inc., Rahway, N.J.

[21] Appl. No.: 227,567

[22] Filed: Aug. 2, 1988

[51] Int. Cl.$^4$ .................. A61K 31/18; C07C 143/78
[52] U.S. Cl. .................. 514/603; 564/87; 546/232; 548/569; 514/331; 514/428
[58] Field of Search .................. 564/87; 514/603

[56] References Cited

U.S. PATENT DOCUMENTS

| | | | |
|---|---|---|---|
| 3,987,199 | 10/1976 | Mrozik | 514/603 |
| 4,603,133 | 7/1986 | Engelhardt et al. | 514/229 |
| 4,731,369 | 3/1988 | Engelhardt et al. | 514/327 |
| 4,845,284 | 7/1989 | Engelhardt et al. | 564/87 |

FOREIGN PATENT DOCUMENTS 1053204 12/1966 United Kingdom .................. 564/87

OTHER PUBLICATIONS

Coleman, *Journal of the National Cancer Institute*, vol. 80, No. 5, pp. 310–317 (1988).

*Primary Examiner*—Glennon H. Hollrah
*Assistant Examiner*—Susan P. Treanor
*Attorney, Agent, or Firm*—Richard S. Parr; Michael C. Sudol

[57] ABSTRACT

A compound of the formula:

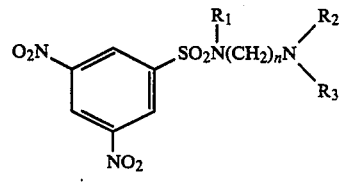

wherein:

n is an integer 2,3,4, or 5; $R_1$ is hydrogen or an alkyl group; and $R_2$ and $R_3$ are defined as follows:

$R_2$ is hydrogen or an alkyl group;

$R_3$ is hydrogen or an alkyl group; or $R_2$ and $R_3$ together form a heterocyclic ring, e.g. piperidine, pyrrolidine.

The compounds have high radiosensitizing activity, and act as agents toxic to hypoxic cells in the absence of radiation.

5 Claims, No Drawings

DINITROBENZENESULFONAMIDES

BACKGROUND OF THE INVENTION

The invention relates to hypoxic cell radiation sensitizers and cytotoxic agents which have high radiosensitizing activity and selective toxicity to hypoxic cells.

U.S. Pat. No. 4,603,133 relates to esters, amides and N-substituted amides of 2-[N-(morpholinoalkyl)aminosulfonyl]-6-nitrobenzoic acids, ued as sensitizers of hypoxic tumor cells to therapeutic radiation. That patent also relates to 2-chlorosulfonyl-6-nitrobenzoate ester prepared as described in U.S. Serial No. 716,886 filed Mar. 27, 1985 and aminating said 2-chlorosulfonylbenzoate ester to produce the corresponding sulfamyl or N-substituted sulfamylnitrobenzoic esters.

U.S. Ser. No. 937,275, filed Dec. 3, 1986, describes 3-nitrobenzenesulfonamides useful in enhancing the effect of therapeutic radiation.

U.S. Ser. No. 937,277, filed Dec. 3, 1986, describes 2-(substituted sulfamyl) derivatives of 4-nitrobenzamide useful for increasing the sensitivity of hypoxic cancer cells to X-rays and gamma-radiation.

U.S. Pat. No. 4,731,369 describes amides and esters of 2-(N-hydroxypiperidinoalkyl) and (hydroxypyrrolidinoalkyl)-aminosulfonyl)-6-nitrobenzoic acids which are useful for treating patients in need of therapeutic radiation.

DETAILED DESCRIPTION OF THE INVENTION

The compounds of the present invention are of the following formula:

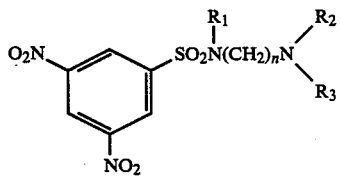

wherein:

n is an integer 2,3,4 or 5;

$R_1$ is hydrogen or an alkyl group; and $R_2$ and $R_3$ are defined as follows:

$R_2$ is hydrogen or an alkyl group;

$R_3$ is hydrogen or an alkyl group; or $R_2$ and $R_3$ together form a heterocyclic ring, e.g. piperidine, pyrrolidine.

Procedures for synthesis of various compounds of the present invention are presented below.

While previous nitrobenzenesulfonamides have been described as effective radiation sensitizers, the dinitro derivative of this invention are selectively toxic to hypoxic cells without radiation. These compounds therefore exhibit properties which make them more effective for cancer treatment.

The method of treatment of human patients or domestic animals undergoing radiation treatment of malignant disease processes employs the compounds of the present invention in pharmaceutical compositions that are administered orally or intravenously, or in depot formulations.

When the compounds are used in conjunction with radiation treatments, the dose employed depends on the radiation protocol for each individual patient. They can be administered from 10 minutes to 5 hours prior to the radiation treatment in a dose of from 0.25 to 4.0 grams per square meter of body surface. The compounds may be employed at intervals during a multi-fraction protocol, and not necessarily with each treatment.

When the compounds are used as cytotoxic agents to hypoxic cells, they can be administered daily in divided-doses up to 0.25 to 4.0 grams per square meter of body surface.

The dosage range given is the effective dosage range and the decision as to the exact dosage used must be made by the administering physician based on his judgment of the patient's general physical condition. In determining the dose for the individual patient, the physician may begin with an initial dose of 0.25 g/square meter of body surface to determine how well the drug is tolerated and increase the dosage with each succeeding radiation treatment, observing the patient carefully for any drug side effect. The composition to be administered is an effective amount of the active compound and a pharmaceutical carrier for said active compound.

The dosage form for intravenous administration is a sterile isotonic solution of the drug. Oral dosage forms such as tablets, capsules, or elixirs may also be used.

Capsules or tablets containing 25, 50, 100 or 500 mg of drug/capsule or tablets are satisfactory for use in the method of tratment of our invention.

The following examples are intended to illustrate but do not limit the process of preparation, product, compositions, or method of treatment aspects of the invention. Temperatures are in degrees Celsius unless otherwise indicated throughout the application.

EXAMPLES

Example 1

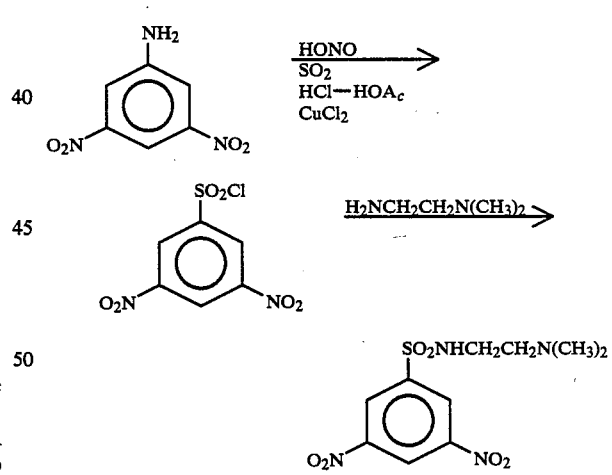

Step A: 3,5-Dinitrobenzenesulfonylchloride

To a suspension of 3,5-dinitroaniline (10.0 g, 55 mmol) in glacial acetic acid (70 mL) and conc HCl (100 mL) cooled to $-5°$ was added slowly, a solution of sodium nitrite (4.07 g, 59 mmol) in water (18 mL). After addition was complete, the mixture was stirred at $-5°$ to $0°$ for an additional 30 min. During this time, a solution of $CuCl_2 \cdot 2H_2O$ (4.43 g, 26 mmol) in water (11 mL) was prepared and added to a cold solution of $SO_2$ (37 g) in glacial acetic acid (74 mL). The diazonium salt solution was then added in portions to the cooled $SO_2$-$CuCl_2$ mixture. After stirring in an ice bath for 3 hours, the reaction mixture was allowed to arm to room temperature and then poured on ice (800 g). The light tan solid was filtered of and dried to give 11.3 g of the sulfonyl chloride, mp 98°-100°.

Step B:
N-(2-Dimethylaminoethyl)-3,5-Dinitrobenzenesulfonamide Hydrochloride A solution of 3,5-dinitrobenzensulfonyl chloride (4.6 g, 17.3 mmol) in dry tetrahydrofuran (130 mL) was added oer 50 min. to a cooled, stirred solution of N,N-dimethyl ethylenediamine (4.0 mL, 34.6 mmol) in tetrahydrofuran (100 mL). After stirring at room temperature overnight, tetrahydrofuran was removed under reduced pressure and the residue flash chromatographed over silica gel. The sulfonamide (5.1 g) was eluted with 5% methanol- 95% chloroform and purified as the hydrochloride salt, mp 238°-40°.

Anal Calcd. for $C_{10}H_{14}N_4O_6S \bullet HCl$: C 33.88; H, 4.26; N, 15.79. Found: C, 34.18; H, 4.47; N, 15.99.

Example 2

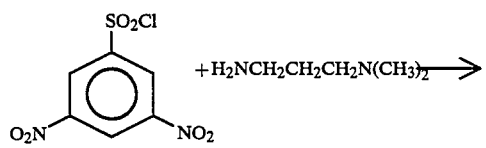

20-25% methanol- 80-75% chloroform gave 6.7 of pure sulfonamide which was further purified by recrystallization of the hydrochloride salt, mp 232°-38° dec, from methanol.

Anal Calcd for $C_{11}H_{16}N_4O_6S \bullet HCl$: C, 35.82, H, 4.65; N, 15.18. Found: C, 35.67; H, 4.64; N, 15.20.

Example 3

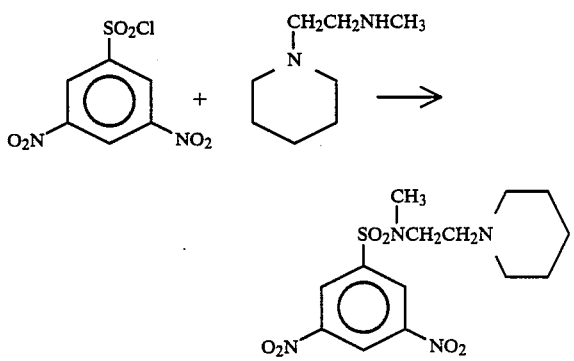

N-(2-Piperidinoethyl)-N-methyl-3,5-dinitrobenzenesulfonamide hydrochloride

By following the same procedure as in Example 2, N-(2-piperidinoethyl)-N-methyl-3,5-dinitrobenzenesulfonamide hydrochloride was prepared from 3,5-dinitrobenzenesulfonyl chloride and N-(2-methylaminoethyl)-piperidine.

Example 4

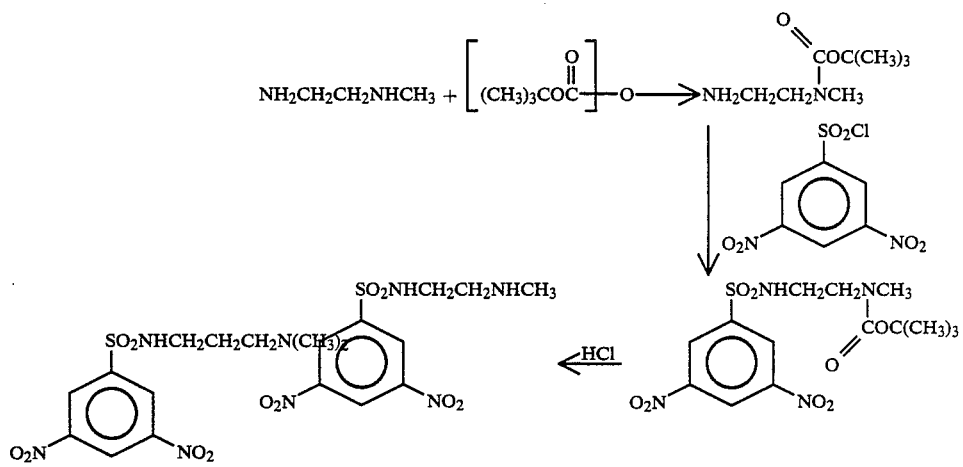

N-(3-Dimethylaminopropyl)-3,5-dinitrobenzenesulfonamide Hydrochloride

A solution of 3-dimethylaminopropylamine (4.9 mL, 39 mmol) and N,N-diisopropylethylamine (6.8 mL, 39 mmol) in tetrahydrofuran (50 mL) was added over 30 min to a cooled, stirred solution of 3,5-dinitrobenzenesulfonyl chloride (10.4 g, 39 mmol) in tetrahydrofuran (175 mL). After addition was complete, the reaction mixture was allowed to warm to room temperature and was stirred at this temperature for 3 hrs. Tetrahydrofuran was removed under reduced pressure and the residue partitioned between ethyl acetate and water. The ethyl acetate extract was washed with brine, dried ($Na_2SO_4$), filtered and concentrated under reduced pressure. Flash chromatography over slica gel and elution with

N-(2-methylaminoethyl)-3,5-dinitrobenzenesulfonamide hydrochloride

Step A:
N-Methyl-N-[2-aminoethyl]tert.-butylcarbamate

A solution of di)tert-butyl) dicarbonate (16.4 g. 75 mmol) in tetrahydrofuran (50 mL) was added over 2 hr to a stirred, cooled solution of N-methylethylenediamine (22 mL, 0.25 mol) in tetrahydrofuran (250 mL). After addition was complete, the reaction mixture was stirred in an ice bath for 1 hour and then at 20°-25° overnight. Solvents were removed under reduced pressure and the residue partitioned between ethyl acetate and brine. The ethyl acetate extract was dried ($Na_2SO_4$), filtered and concentrated to give 13.5 g of crude product. Flash chromatography over silica gel and elution with 20% methanol- 80% chloroform gave 9.9 g of the desired mono BOC protected diamine.

Step B: N-(2-(N-Tert-butoxycarbonyl-N-methylamino) ethyl)-3,5-dinitrobenzenesulfonamide A solution of N-methyl-N-[2-aminoethyl]tert.butyl-carbamate (0.33 g, 1.88 mmol) and N,N-diisopropyle-thylamine (0.33 mL, 1.88 mmol) in tetrahydrofuran (5 mL) was added oer 5 min to a stirred, cooled solution of 3,5-dinitrobenzenesulfonyl chloride (0.50 g, 1.88 mmol) in tetrahydrofuran (10 mL). After stirring at 20°–25° for 20 hours, tetrahydrofuran was removed under reduced pressure and the residue partitioned between ethylace-tate and water. The organic extract was dried ($Na_2SO_4$), filtered and concentrated. Flash chromatography of the residue over silica gel and elution with chloro-form gave 0.30 g of product. An analytical sample, mp 175.0°–177.0° was obtained by recrystallization rom ethyl acetate-hexane.

Anal. Calc'd for $C_{14}H_{20}N_4O_8S$: C, 41,58; H, 4.99; N, 13.86. Found: C, 41.71; H, 5.24; N, 14.07. Step C: N-(2-Methylaminoethyl)-3,5-dinitrobenzenesulfonamide Hydrochloride A solution of the protected sulfonamide from Step B (0.30 g) in ethyl acetate (30 mL) was cooled in an ice bath and saturated with anhydrous hydrogen chloride for 5 min. After stirring in the ice bath for 20 min and then at 20°–25° for 20 min, solvents were removed under reduced pressure. The residue was recrystallized from a water-methanol-ethyl acetate-hexane mixture to give 0.20 g of product, mp 248°–51° dec.

Anal. Calc'd for $C_9H_{12}N_4O_6S\cdot HCl$: C, 31.72; H, 3.84; N, 16.44. Found: C, 31.58; H, 3.76; N, 16.48.

What is claimed is:

1. A compound of the following formula:

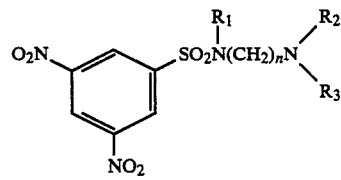

wherein:
n is an integer 2, 3, 4 or 5;
$R_1$ is hydrogen or a methyl group;
$R_2$ is hydrogen or a methyl group;
and $R_3$ is hydrogen or a methyl group.

2. The compound of claim 1 which is:

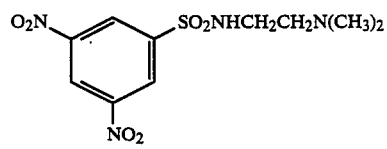

3. The compound of claim 1 which is:

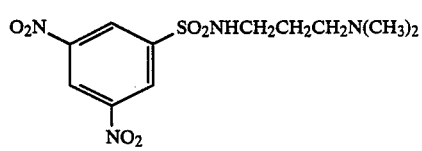

4. The compound of claim 1 which is:

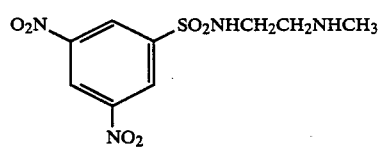

5. A pharmaceutical composition for enhancing the therapeutic effect of radiation which consists of an effective amount of a compound defined in claim 1 and a non-toxic pharmaceutically acceptable carrier.

* * * * *